US009922169B1

(12) United States Patent
Candy

(10) Patent No.: US 9,922,169 B1
(45) Date of Patent: Mar. 20, 2018

(54) DIGITAL COMMAND PROMPTING DEVICE FOR DEMENTIA PATIENTS

(71) Applicant: Katrina Goff Candy, Echua (AU)

(72) Inventor: Katrina Goff Candy, Echua (AU)

(73) Assignee: MINDGO PTY LTD, Yarraville, Victoria (AU), AS TRUSTEE FOR THE MINDGO UNIT TRUST ( * ) Notice: Subject to any disclaimer, the term of this patent is extended or adjusted under 35 U.S.C. 154(b) by 0 days.

(21) Appl. No.: 15/607,516

(22) Filed: May 28, 2017

(51) Int. Cl.
| G06F 19/00 | (2018.01) |
| H04B 1/3827 | (2015.01) |
| G06F 3/0481 | (2013.01) |
| H04W 4/22 | (2009.01) |
| H04W 64/00 | (2009.01) |

(52) U.S. Cl.
CPC ......... *G06F 19/3418* (2013.01); *H04B 1/385* (2013.01); *G06F 3/0481* (2013.01); *H04W 4/22* (2013.01); *H04W 64/00* (2013.01)

(58) Field of Classification Search
CPC ... G06F 19/3418; G06F 3/0481; H04B 1/385; H04W 4/02; H04W 4/22; H04W 64/00; G06Q 10/109; G06Q 10/1095; H04L 67/1097; H04L 67/22; H04M 3/565; A61B 5/0022; A61B 5/0024; A61B 2562/0219; A61B 5/024; A61B 5/1112; A61B 5/14532; A45F 2005/008
See application file for complete search history.

(56) References Cited

U.S. PATENT DOCUMENTS

| 2007/0277120 A1* | 11/2007 | Wilson | G06F 1/1626 715/808 |
| 2010/0053867 A1* | 3/2010 | Ellis | A61B 5/1038 361/679.03 |
| 2010/0056340 A1* | 3/2010 | Ellis | A61B 5/1038 482/4 |
| 2010/0057951 A1* | 3/2010 | Ellis | A61B 5/1038 710/33 |
| 2010/0062740 A1* | 3/2010 | Ellis | A61B 5/1038 455/351 |
| 2011/0265038 A1* | 10/2011 | Okogun | G06Q 10/107 715/823 |
| 2013/0013710 A1* | 1/2013 | Wilson | G06F 1/1626 709/206 |
| 2013/0190907 A1* | 7/2013 | Ellis | A61B 5/1038 700/91 |
| 2013/0253819 A1* | 9/2013 | Ellis | A61B 5/1038 701/428 |

(Continued)

*Primary Examiner* — Orlando Bousono
(74) *Attorney, Agent, or Firm* — Robert J. Craig

(57) ABSTRACT

The digital command prompting device and computer system for dementia patients is an aide to help all people, but especially those who have special needs particularly individuals who have diminished or diminishing function of their brain because of dementia. The device is predominately mobile but can also be stationary and can be programmed by receiving and selecting pre-set commands to operate and assist a user with their daily living standards or needs and interacts with a central data base computer system having administrative and carer internet web page interfaces. The device may be used within the home environment, outdoor environment or a restricted environment, e.g. aged care facility, hospital, preschool or school.

8 Claims, 19 Drawing Sheets

(56) References Cited

U.S. PATENT DOCUMENTS

| | | | | |
|---|---|---|---|---|
| 2014/0094941 A1* | 4/2014 | Ellis | ............... | A61B 5/1038 700/91 |
| 2014/0097967 A1* | 4/2014 | Ellis | ............... | A61B 5/1038 340/870.07 |
| 2015/0242585 A1* | 8/2015 | Spiegel | ............... | G06F 19/3418 705/2 |
| 2015/0248844 A1* | 9/2015 | Ellis | ............... | A61B 5/1038 434/247 |
| 2015/0281927 A1* | 10/2015 | Fiedler | ............... | H04W 4/22 455/404.2 |
| 2015/0347986 A1* | 12/2015 | Gilzean | ............... | G06Q 10/109 455/416 |
| 2016/0107033 A1* | 4/2016 | Ellis | ............... | A61B 5/1038 434/247 |
| 2016/0129309 A1* | 5/2016 | Ellis | ............... | A61B 5/1038 434/254 |
| 2016/0192128 A1* | 6/2016 | Gilzean | ............... | G06Q 10/109 455/456.3 |
| 2017/0311904 A1* | 11/2017 | Davis | ............... | A61B 5/746 |

\* cited by examiner

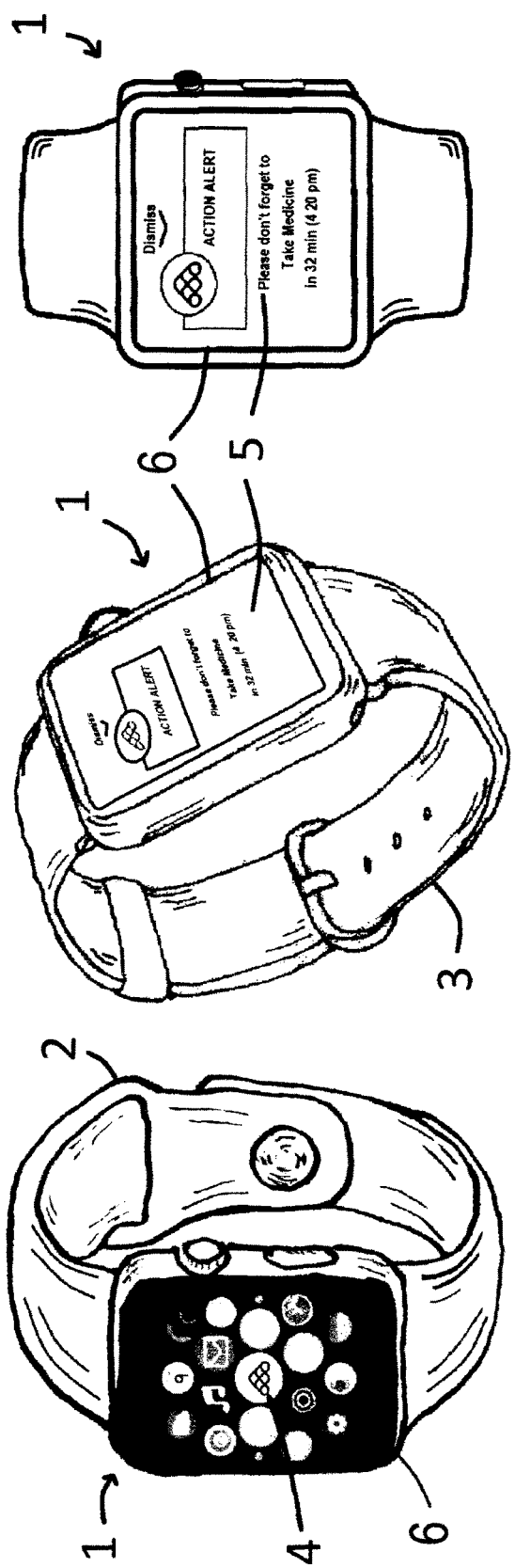

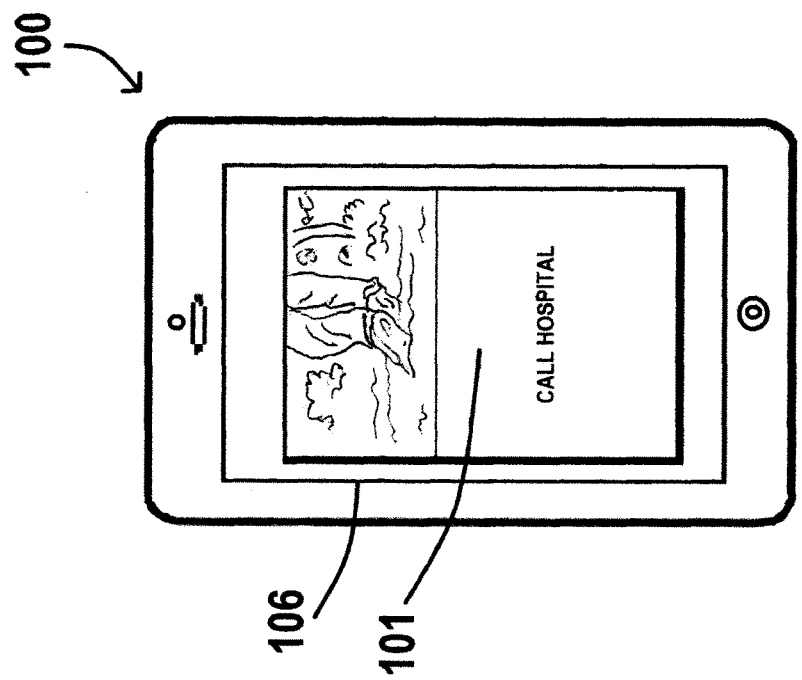
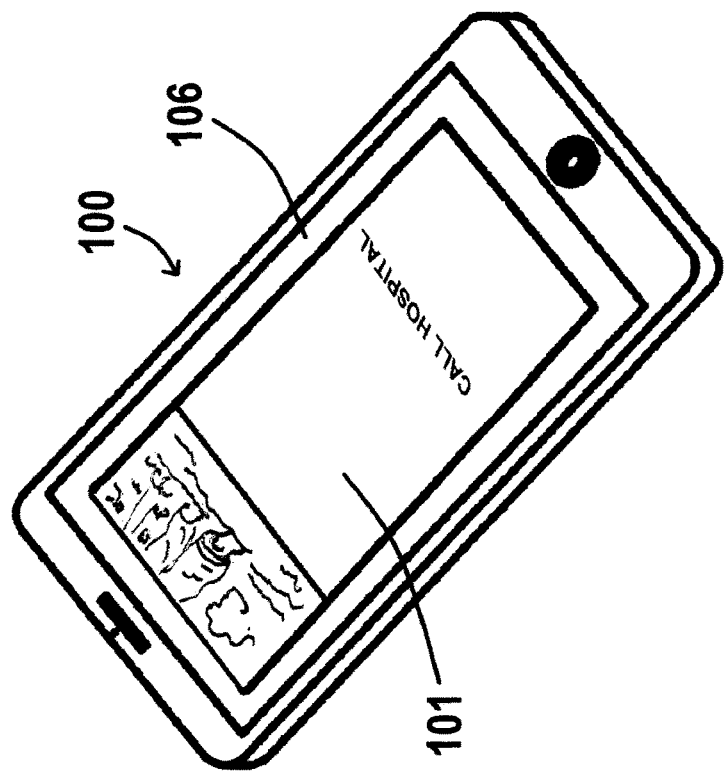
Fig. 2B
Fig. 2A

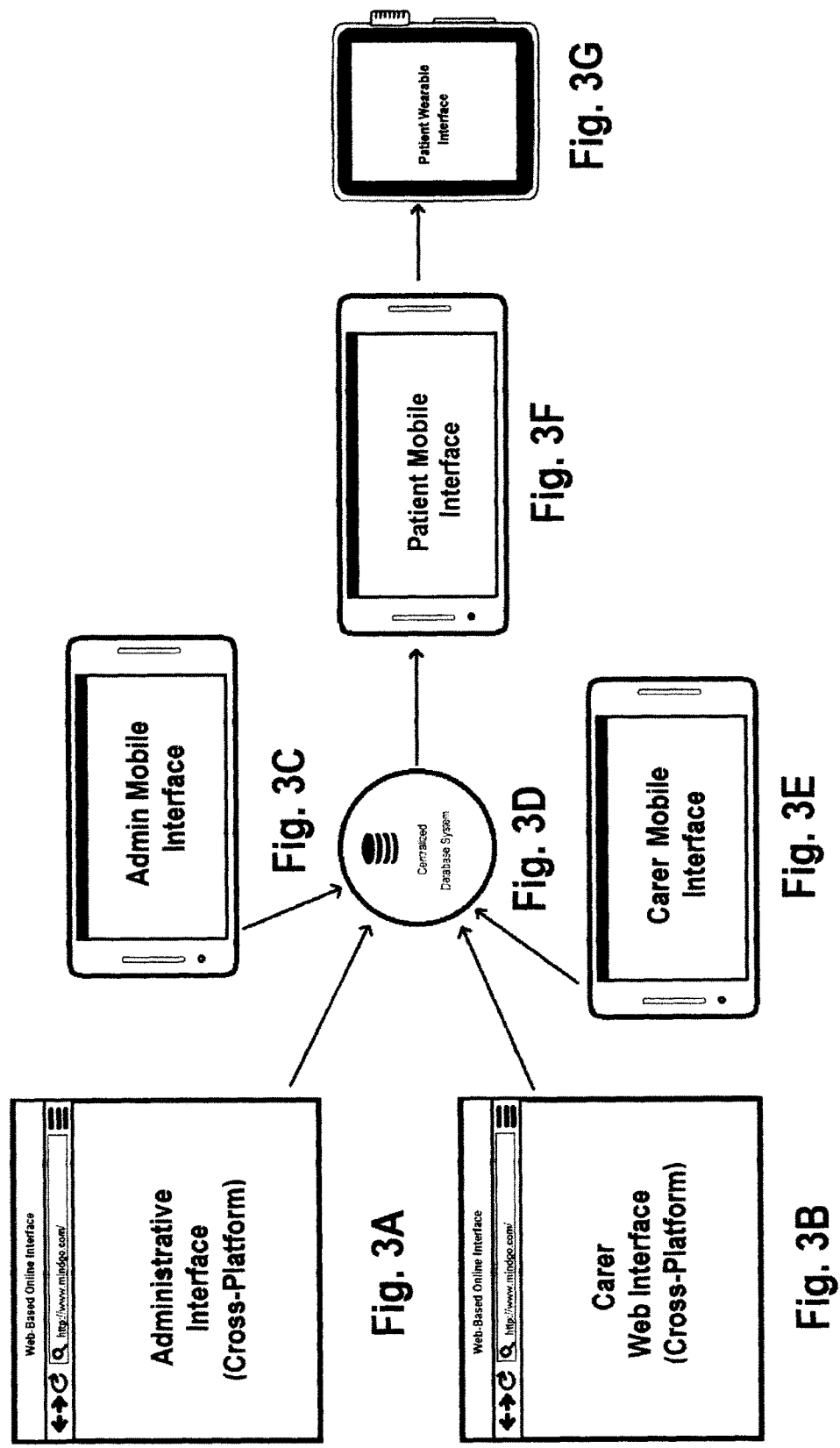

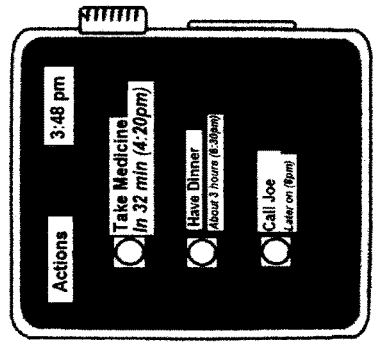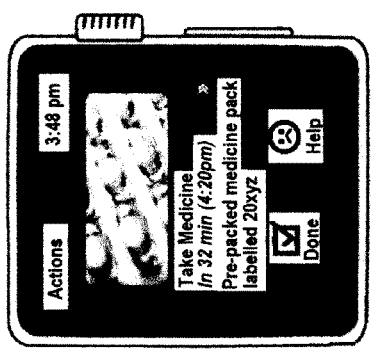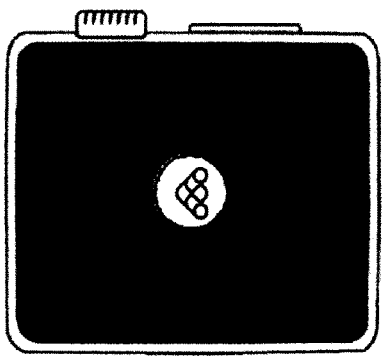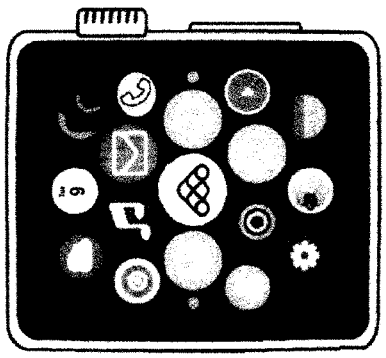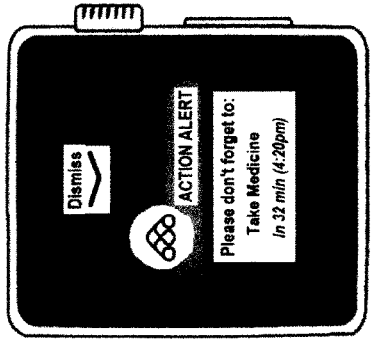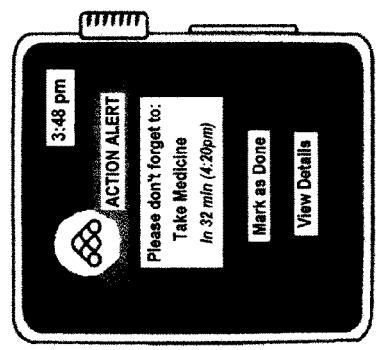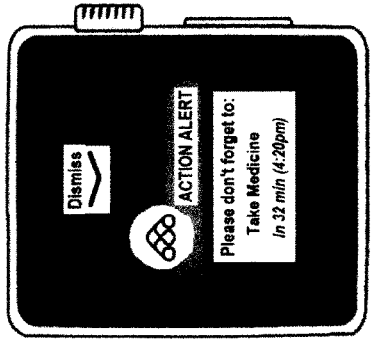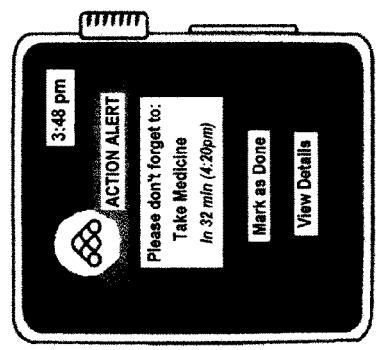

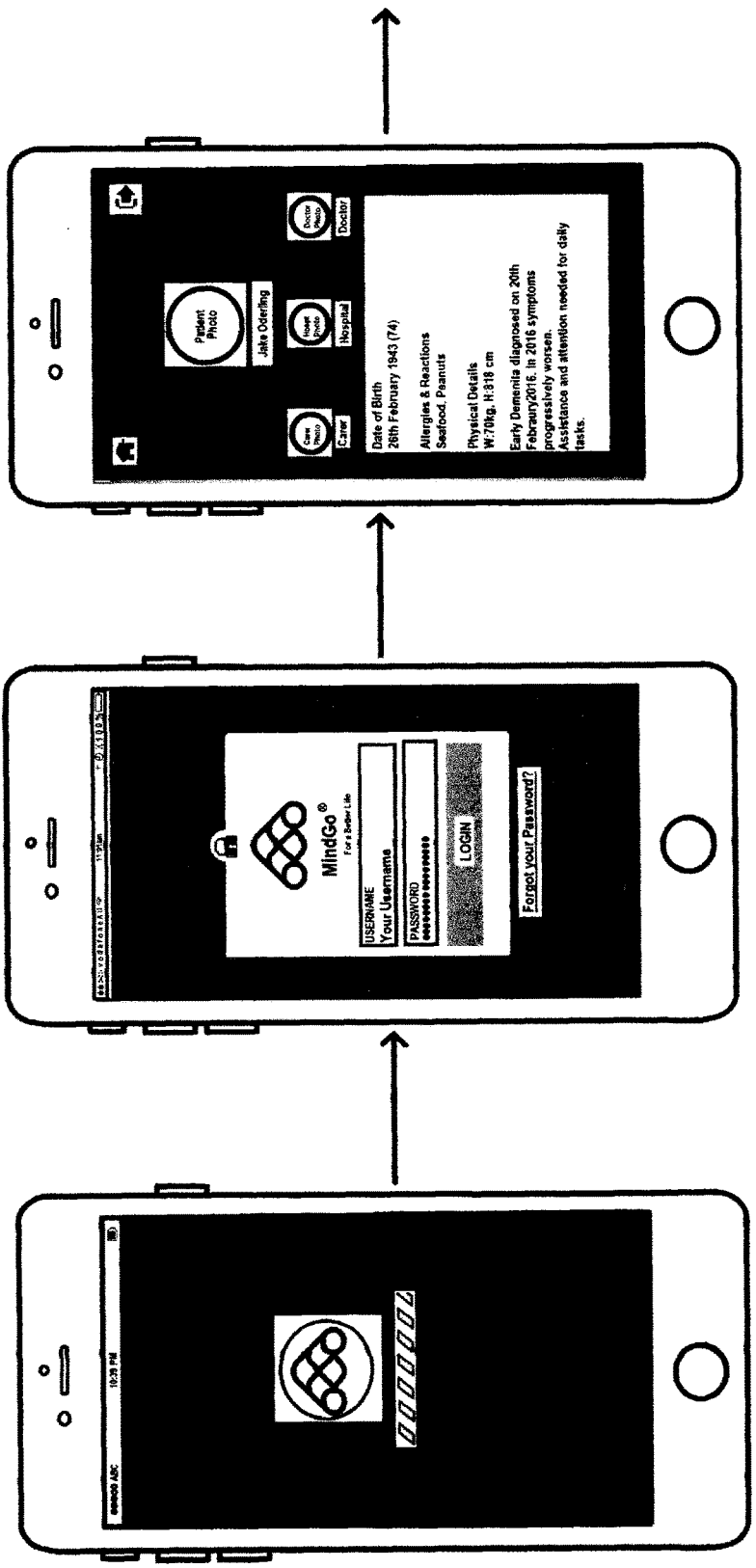

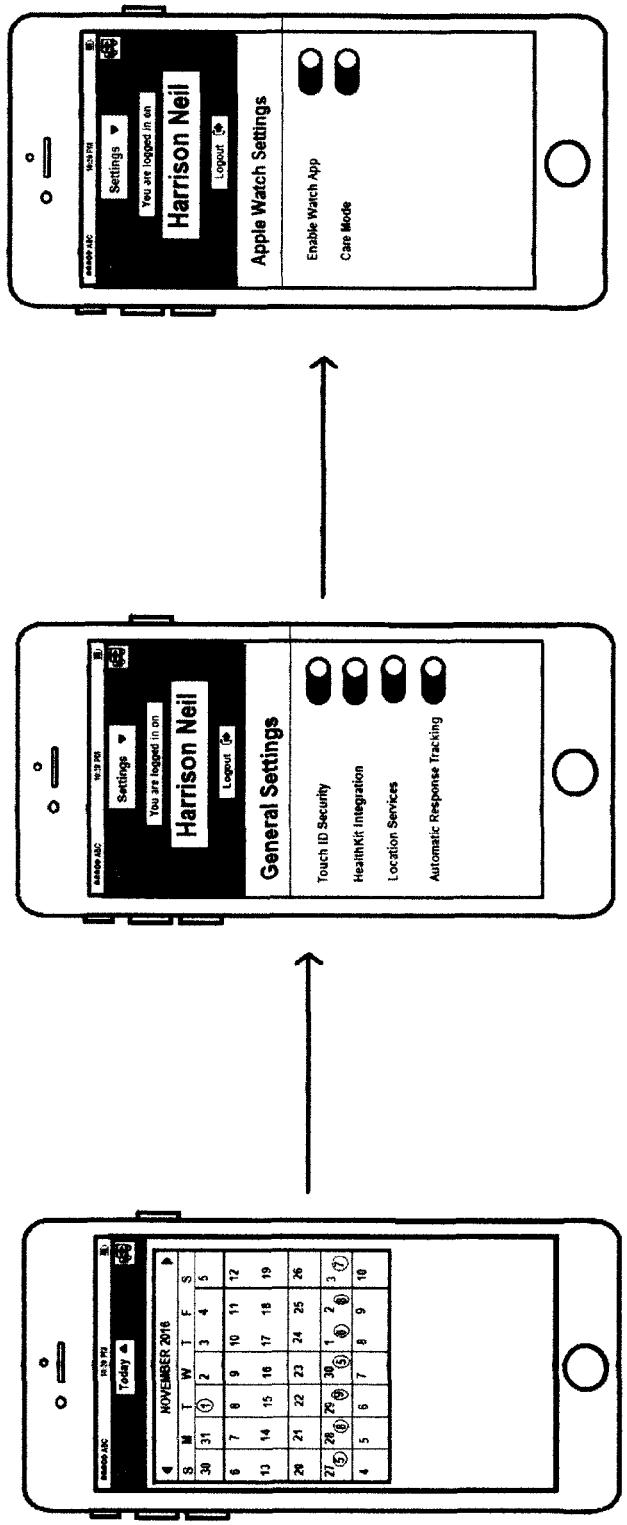

DIGITAL COMMAND PROMPTING DEVICE FOR DEMENTIA PATIENTS

CROSS-REFERENCE TO RELATED APPLICATIONS

This application is a continuation-in-part application of U.S. non-provisional utility patent application Ser. No. 15/256,503 filed Sep. 2, 2016.

FEDERALLY SPONSORED RESEARCH AND DEVELOPMENT

None.

APPENDICES

None.

BACKGROUND OF THE INVENTION

Dementia itself is not a disease but is caused by lots of different diseases and the word 'dementia' is an umbrella term for the symptoms caused by these diseases such as memory loss, confusion, and personality change. Alzheimer's disease is the most common cause but other dementias include vascular dementia, dementia with Lewy bodies and frontotemporal dementia.

Dementia is not an inevitable part of getting older and although a majority of people with dementia are over 65, the condition is not a normal part of getting older. The likelihood of developing dementia rises with age, but it's not a given that an older person will develop it. In the United Kingdom, for example, over 40,000 people under the age of 65 have dementia.

Dementia has a bigger impact on women with more and more women living well into their 80s and half a million women in the United Kingdom are now living with dementia and the condition is the leading cause of death in women in the United Kingdom. In addition, women are also more likely to take on unpaid caring roles for other people with dementia and are more than twice as likely as men to provide intensive, 24-hour care for individuals for dementia related conditions.

Dementia is a global issue even though it is a common myth that dementia is only an issue in the western world. The largest increases in dementia expected over the next 20 years are in places like China, India and Sub-Saharan Africa. Dementia is a truly global health issue, affecting 46.8 million people worldwide.

Dementia is more than just memory loss and although most people associate dementia with memory loss, the condition affects people in a wide variety of ways. For example, these might include changes in behavior, confusion, disorientation, delusions, hallucinations, difficulty communicating, problems judging speeds, distances and even cravings for particular foods. Everyone's experience of dementia is different and there are no treatments to stop the diseases that cause dementia and while some treatments can help people to live with their symptoms a little better, there are no treatments that slow or stop diseases like Alzheimer's. Consequently, this means that the diseases will continue to get worse over time unless new treatments can be found quickly.

A person diagnosed with dementia will have contact with a number of health professionals, usually over a long period of time. This will most likely include the family doctor, medical specialists, therapists, community nurses, and social workers all of whom are potential carers for dementia patients. The degenerative nature of dementia means that families and carers will also have a lot of contact with these health professionals and as the disease in an individual progresses these contacts will almost certainly increase.

Usually the family doctor provides on-going health care, sometimes for both the person with dementia and the family and other carers. This means that the relationship between the doctor, the person with dementia and family and carers is critical. The system and devices of the instant invention, it is believed, will reduce the workload of the family doctor assisting a dementia patient and provide extra help for the carers of these patients.

Today, there are more than 200,000 Australians providing informal unpaid assistance to people with dementia and the vast majority of people with dementia living in the community (91%) rely on an informal carer to support them. Most informal carers are either the spouse or adult child of the person with dementia and nearly a quarter of people with dementia living in the community (22%) rely solely on informal care and do not access any formal care services. Additionally, 81% of co-resident informal carers provide more than 40 hours of care per week for dementia patients. Future projections such as Access Economics projects that by 2029 there will be a shortage of 94,266 full-time equivalent (FTE) family carers. It is further estimated the current cost of replacing family carers with paid carers is $5.5 billion per year.

Therefore, the impact of caring can be enormous, for example, caring for a person with dementia can lead to increased rates of depression, stress and anxiety for carers compared to non-carers. For example, in Australian surveys of carers, 31% of respondents reported that caring for the person with dementia had a negative impact on their physical health (3), and 34% reported feeling weary or lacking in energy. Additionally, the stress of caring may result in impaired immunity, high levels of stress hormones, hypertension (high blood pressure) and an increased risk of cardio-vascular disease for carers.

Additionally, the demands of caring for someone with dementia have been shown to put carers at risk of social isolation. A National Carer Survey in the United States found that carers of people with dementia were more likely to report giving up their holidays or hobbies, having less time for family, having more family conflicts and work related problems.

Additionally, caring for dementia related patients can also have significant financial impacts. According to the Dementia in Australia report, 54% of carers of people with dementia (and 45% of primary carers) are of working age while only 56% of these (and 38% of primary carers) were employed at the time of the survey.

The system and devices of the instant invention, known as the MindGo, trademark pending, system and devices, fundamentally use a prompting software developed to remind the user not to forget important tasks, events, time slots or memories that make up the unique life cycle of the user. The software can also be used to store memories, update medical information and link fragmented threads of memory together, of the user, to maintain a level of independence for those living with Alzheimer's and dementia.

SUMMARY OF THE INVENTION AND PRIOR ART

For the purposes of the following disclosure, the term "patient" denotes a person who has been diagnosed with or identified as having dementia or similar conditions, for example, Alzheimer's disease, and for whom medical care has been prescribed and/or identified while the term "user" denotes a person who has been identified to be a patient and who is using the system and/or devices as described in the instant invention; occasionally, in the disclosure, the term "patient/user" is used to denote a "patient" or a "user". Similarly, the term "carer" refers to any number of health professionals or other individuals involved with providing any time of care, mental, physical, or otherwise for a "user" and/or "patient" and an "administrator" is a person supervising a number of carers. Additionally, the terms "prompt" and "command", "command prompt", for purposes of this disclosure are synonymous and refers to information, instructions or reminders, from the MindGo system and devices, to the user to perform a certain task.

There exists in the prior art medical alert devices used to assist people, usually elderly or disabled, which devices act to contact or communicate with emergency medical facilities in the event a person has a traumatic medical event. This event may be a fall where the person is unable to right themselves, or when they have a stroke or heart attack disabling them from verbally calling for help. These medical alert devices usually consist of a small device attached to a lanyard or other cord necklace to allow the device to be worn by a user and the device usually has a single button to be pushed by the user. The button can then activate a communication component for directing connecting with emergency medical facilities. These medical alert devices however are usually a single function apparatus and usually lack any other capabilities for assisting a user.

These is a need for a system and device which has the capability both to act as a medical alert device but additionally can be used to assist a person through their entire daily and nightly routines by prompting them at the appropriate times to perform certain tasks. There is a particular need for individuals of diminished mental or brain function, either because of being of young age, for example, a preschooler, or for elderly individuals whose mental or brain function is diminishing because of age. The device and system should further be capable of being used by visually or hearing impaired, handicapped or mute individuals The system and device should further be provided with an alarm feature in the form of a prompt, for example, a vibrator or sounder which signals the user to perform a certain task; the device should be able to continue to repeat to vibrate or sound an alarm to get the attention of the user. If after a certain time frame there is no response from the user, the device should switch over to a medical alert signal which is transmitted to a medical alert staff desk, nursing station or emergency office or facility.

The instant invention comprises a computer system, the MindGo, trademark pending, hereinafter "the MindGo system", and digital command prompting devices, the MindGo devices, hereinafter "the MindGo devices", to assist and help people with medical needs and assistance, particularly of dementia related conditions, i.e., patient.

The MindGo system and devices are especially constructed for those people who have special medical needs, such as those with dementia, Alzheimer's disease, or similar age related conditions. The MindGo computer system is provided with a centralized database constructed to electronically interact, via wired or wireless electronic communication network, with a centralized computer system. The MindGo system and devices are further provided with computer administrative internet web page interfaces, the MindGo administration interfaces, and carer internet web page interfaces, the MindGo carer interfaces, which allow for the programming of user MindGo mobile devices for receiving and selecting pre-set commands to operate and assist a user to help them with all aspects of their daily living. The whole MindGo system, and MindGo devices, are operated by computer application software, hereinafter "the MindGo app", constructed to operate the MindGo computer system and devices. The administrators using the MindGo administrative internet web page interfaces are known as MindGo administrators and carers using the carer internet web page interfaces are known as MindGo carers.

The MindGo system and devices are further constructed to either be mobile or stationary and may come in various applications, particularly mobile smartphones, or wearable watches, all provided with the MindGo app. The MindGo watch device is also constructed to be fitted to a wrist bracelet or watch band such that it can be worn in any environment.

The MindGo app is constructed to be used with any smartphone and as with any smartphone it can be stationary and sited beside a bed of a user or can also be fitted to be used in an automobile.

Although the MindGo system and devices are primarily constructed for a user with special medical needs, as discussed above, it can also be used for a functional but forgetful user and depending on the degree of the diminishing thought process of a forgetful user which may vary due to their capacity during the day and may cause them to become tired or confused, the commands of the MindGo device may increase these type of individuals with their efficiency.

The MindGo system and devices are also capable of being programmed to accommodate any type of physical or mental user disability and they are constructed with daily-calendars as a reminder for the user, e.g., to collect their newspaper or weekly calendar reminder, e.g., Tuesday garbage put the bins out on street. The MindGo system and devices can also inform the user of activities available in the nursing home or the location of various sections of a hospital, e.g., the x-ray department, which the user may need. The MindGo system and devices can also be used to remind the user of appointments with doctors which can be pre-set via voice application in MindGo device command.

The MindGo system and devices are further constructed to be used in an aged care facility and can assist the user and facility staff by allowing them to perform his/her own tasks. Similarly, the MindGo system and devices can be used as an assessment tool for the user in place of a person being assessed by a facilitator especially when the user becomes cagey and try to prove they are still 100% okay when the user realizes that they are faltering, mentally or physically, and the user may try to hide this fact from facility staff. The assessment feature/tool can assess a mental or physical competence level of the user for staff doctors or specialists without the awareness of the user. Additionally, the MindGo system and devices can assist in crime protection preventing the user from becoming an "easy target" for criminals.

The MindGo system and devices are also provided with an alarm component which can be in the form of a sounder and/or vibrator capable of communicating with the user. This alarm component is further capable of alerting the user of instant messages as the capacity of the user diminishes.

The MindGo system and devices are further provided with a voice activation component and/or a picture display prompts to be used by a user unable to read. The voice activation component is particularly useful for a visually impaired user.

As previously discussed, the MindGo app spans across the MindGo computer system and devices prompting users to complete everyday tasks that elude them as the symptoms of dementia take hold. Additionally, the MindGo system and devices are designed to build up a basic platform of health and physical information about the user while the user takes advantage of the prompting abilities of the MindGo app to better cope with their Dementia or degrading conditions. As every individual is unique the MindGo system and devices will intelligently collate data and behavioral patterns over time to better serve each of its users as well as better assist their carers and administrators.

Every user has a set of daily tasks that form the structure of their days and weeks to assist them with routine tasks which they may otherwise forget due to Dementia or associated conditions. These tasks will have due date/times so that the individuals can keep track of the date, the time of day, what they need to do next and what they need to tick off their list as they complete each of the tasks. For those users who are at a much more advanced level of dementia the tasks will be ticked off by their carer, using the MindGo system and devices, to aid in the daily management of the user. This basic yet methodical system keeps track of the users and is used to assess their progress at different intervals of the disease. The aim is to provide a digital record of every user who uses the MindGo system and devices and the difficulties that they experience will eventually help medical professionals to better understand the symptoms at every stage of their disease or condition and hopefully increase the chances of eradicating the disease or condition in the future.

With the MindGo system and devices, every user is provided with either a MindGo smartphone and/or wearable watch for the prompting features to work optimally. The sensation or vibration will prompt haptic feedback, and sound alert the user to perform a particular task during the day as often as required. For example, an alert may remind the user "Take your medication now Bob", the user, and Bob will then have to tick off the task once he completes it to remove the task from the list of tasks for the specific day. The carer must do the same if the user is unable to or not in the right frame of mind to understand the prompt.

There are other benefits of the MindGo system and devices. For example, if a care giving center or aged care center have rostered staff taking care of multiple patients daily, they will have the ability to identify which carer signed off on the tasks of any given user/patients. This ease the transition when onboarding new carer staff as they will have a diarized set of instructions that they can follow for each user/patient.

BRIEF DESCRIPTION OF THE DRAWINGS

FIGS. 1, 1A, 1B and 1C disclose a first embodiment of a MindGo device 1.

FIGS. 2, 2A and 2B disclose a second embodiment of a MindGo device 100.

FIGS. 3, 3A, 3B, 3C, 3D, 3E, 3F, and 3G are an overall system architecture schematic for the MINDGO system and devices of FIGS. 1, 1A-1C, and 2, 2A-2B.

FIGS. 5, 5A and 5B are a part schematic of the MindGo system internet web page administrative interface for the MindGo system and devices of FIGS. 1, 1A-1C, and 2, 2A-2B.

FIGS. 6, 6A and 6B are an additional schematic of the MindGo system internet web page administrative interface for the MindGo system and devices of FIGS. 1, 1A-1C, and 2, 2A-2B.

FIGS. 7, 7A and 7B, are an additional schematic of the MindGo system internet web page administrative interface for the MindGo system and devices of FIGS. 1, 1A-1C, and 2, 2A-2B.

FIGS. 8, 8A and 8B are a part schematic of MindGo system internet web page carer interface for the MindGo system and devices of FIGS. 1, 1A-1C, and 2, 2A-2B.

FIGS. 9, 9A and 9B are an additional schematic of MindGo system internet web page carer interface for the MindGo system and devices of FIGS. 1, 1A-1C, and 2, 2A-2C.

FIGS. 10, 10A and 10B are an additional schematic of MindGo system internet web page carer interface for the MindGo system and devices of FIGS. 1, 1A-1C, and 2, 2A-2B.

FIGS. 11, 11A and 11B are an additional schematic of MindGo system internet web page carer interface for the MindGo system and devices of FIGS. 1, 1A-1C, and 2, 2A-2B.

FIGS. 15, 15A, 15B, 15C, 15D, 15E, 15F, 15G, and 15H are a schematic of the MindGo device of FIGS. 1, 1A-1C.

FIGS. 16, 16A, 16B, and 16C are a part schematic of the MindGo device of FIGS. 2, 2A and 2C.

FIGS. 17, 17A, and 17B are an additional schematic of the MindGo device of FIGS. 2, 2A and 2b.

FIGS. 18, 18A, and 18B are an additional schematic of the MindGo device of FIGS. 2, 2A and 2B.

FIGS. 19, 19A, 19B and 19C are an additional schematic of the MindGo device of FIGS. 2, 2A and 2B.

DETAILED DESCRIPTION OF THE INVENTION

Figure 4:
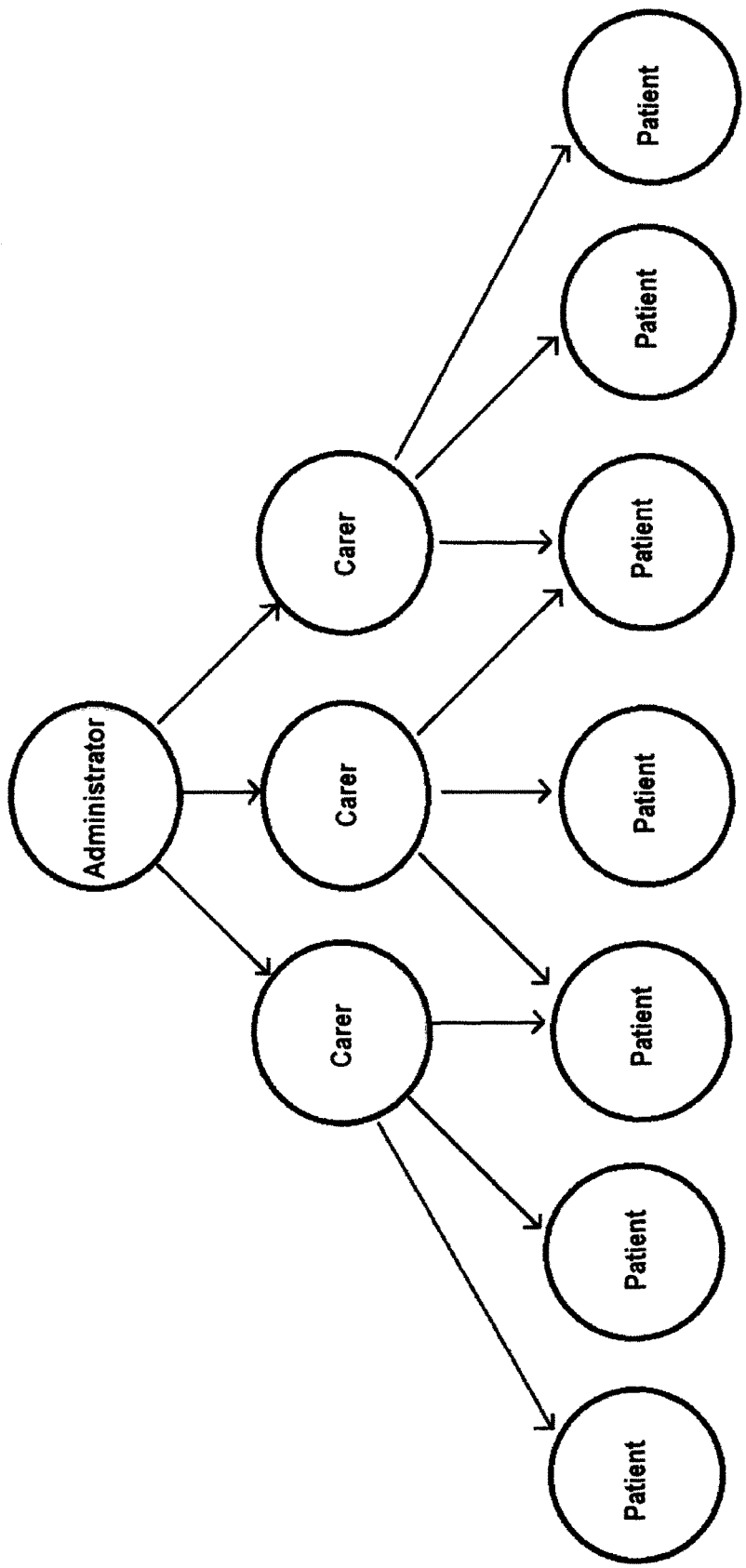
FIG. 4 is a schematic of the MindGo system roles and relationships for the MindGo system and devices of FIGS. 1, 1A-1C, and 2, 2A-2C.

FIG. 1 shows a first embodiment of the MindGo device 1 in the form of a digital watch similar to an Apple™ watch which is worn on the wrist of a user.

Particularly, FIG. 1A shows a three-quarters right handed perspective view of the MindGo device 1 being attached to wrist band 2. Further, as is discussed in further detail in reference to FIG. 15, the MindGo system is provided with a computer processing application software, i.e., otherwise known as "the MindGo app", which app is capable of processing any signal, data or input from the MindGo device 1 and the MindGo app is capable of producing display or command prompts. In the example of FIG. 1B, it is the prompt "Action Alert" to inform, remind or command the user to perform a certain task. For the MindGo device 1, the MindGo app is referred to as a watch MindGo app and in FIG. 1A, the watch MindGo app display 4 is discussed in detail in relation to FIGS. 15G and 15H shown on screen 6 of the MindGo device 1.

FIG. 1B discloses a three-quarters left handed perspective view of the MindGo device 1 attached to a different configured wrist band 3 and a watch MindGo app action alert reminder display 5, which is discussed in further detail in relation to FIGS. 15G and 15H.

FIG. 1C shows a front view of the MindGo device 1 with the watch MindGo app action alert reminder display 5. Also MindGo device 1 is capable of electronically communicating with mobile phone telecommunications networks to connect the MindGo device 1 to the MindGo computer system as well as to GPS and GLONASS satellite systems for allowing location of wearer of the device, i.e., the user. It is also to be noted that MindGo device 1 is capable of electronically connecting with and communicating, by wireless signals, as is disclosed and discussed below, with the MindGo electronic computer system which includes administrative internet web page interfaces as well as carer internet web page interfaces as discussed in reference to FIGS. 5-12, supra. The watch MindGo app uses the connectivity with the administrative and carer interfaces to remind and prompt users using appropriate haptic feedback in order to better remind the administrator, carer, and/or user of tasks that need completing, especially those of importance or which are health critical. Also contacts can be accessed and emergency calls can be placed if required all remotely through the watch MindGo app. Additionally, the watch MindGo app is vital for those patients that do not always carry or want to have their smartphone within reach; as the wearable MindGo device 1 can always be on their wrist the user is able to access and action feedback directly without ever picking up their smart phones. It is further to understood that although FIG. 1 discloses the MindGo device 1 as being used with an Apple™ digital watch, any similar digital watch could be used. It is also to be noted the type of wrist band used with the MindGo device 1 may vary depending on user desires.

FIG. 2 discloses another embodiment of the MindGo device 100 in the form of a smartphone similar to an Apple™ iPhone. As with MindGo device 1, MindGo device 100 is capable of connecting with the MindGo system provided with a computer processing application software, i.e., otherwise known as the "MindGo app", which app is capable of processing any signal, data or input from the MindGo device 100 and this app is capable of producing display or command prompts on MindGo device 100. Also MindGo device 100 is capable of electronically communicating with mobile phone telecommunications networks to connect MindGo device 100 to the MindGo computer system as well as to GPS and GLONASS satellite systems for allowing location of wearer of the device, i.e., the user. FIG. 2A shows a three-quarters right handed perspective view of MindGo device 100 with a typical software application reminder display 101. FIG. 2B shows a front view of the MindGo device 100 with the app action alert reminder display 101 shown of screen 106. It is also to be noted that as with MindGo device 1, MindGo device 100 is capable of electronically connecting with and communicating, by wireless signals, as is disclosed and discussed below, with the MindGo computer system which includes administrative internet web page interfaces as well as carer internet web page interfaces as discussed in reference to FIGS. 5-12, supra. Further, the MindGo device 100 app, similar to the MindGo app of MindGo device 1, uses the connectivity with the administrative and carer interfaces to remind and prompt patients/users using appropriate haptic feedback in order to better remind them of important or critical health tasks that need completing along with contact and emergency call capability. Finally, it is further to understood that although FIG. 2 discloses the MindGo device 100 as being used with an Apple™ iPhone, any similar smartphone can be used.

In FIG. 3 the overall system architecture for the MindGo system is disclosed. Particularly, FIG. 3 discloses that the system consists of two internet web page interfaces, as shown in FIG. 3A, the administrative internet web page interface for administering all carers and patients/users and as shown in FIG. 3B, the carer internet web page interface, which allows carers to login to manage users. The users have their own mobile app interface, as shown in FIG. 3F, their smartphones, i.e., MindGo device 100 as discussed in reference to FIG. 2. Additionally, there is an optional extension, as shown in FIG. 3G, on their wearable watch, MindGo device 1, discussed in reference to FIG. 1. The administrative internet web page interfaces and internet web page carer interfaces are displayed on stationary computer components or laptop computers but can employ, and be displayed on mobile components, such as electronic tablets or smartphones, as shown in FIGS. 3C and 3E. All of the above interfaces are connected in real-time to a centralized database system as shown in FIG. 3D which propels and supports all data exchanges in real-time requested by each of the above interfaces.

FIG. 4 is a detailed figure of MindGo system shows the interrelationship of the roles of the various individuals. Particularly, FIG. 4 discloses the different roles that exist in the MindGo system, the administrator, the carer, and the patient. At the top level are the high-level administrators who can have an infinite number of carers they administer and control, while each carer can also have an infinite number of patients under them that they manage and care for. In addition, each patient can have multiple carers, as an example, a carer could be a relative and another being their doctor. And although administrators can in theory manage all carers at their level, a carer can only manage patients assign to them. Administrators can assign existing patients to designated carers and finally, the administrators have absolute and overall control over all carers and patients, their assignments and relationships.

FIGS. 5 to 8 discloses various pages of the MindGo internet web page administrative interface and particularly shows the various computer windows available to the administrators to assist and enable them to manage, oversee and control carers as well as their patients. The administrator interface is not designed to manage in-depth details of the patients but rather manage them at a higher level relative with the carers, along with certain and specific moderation tasks that may require intervention or overriding carer occasionally.

Figure 5B:
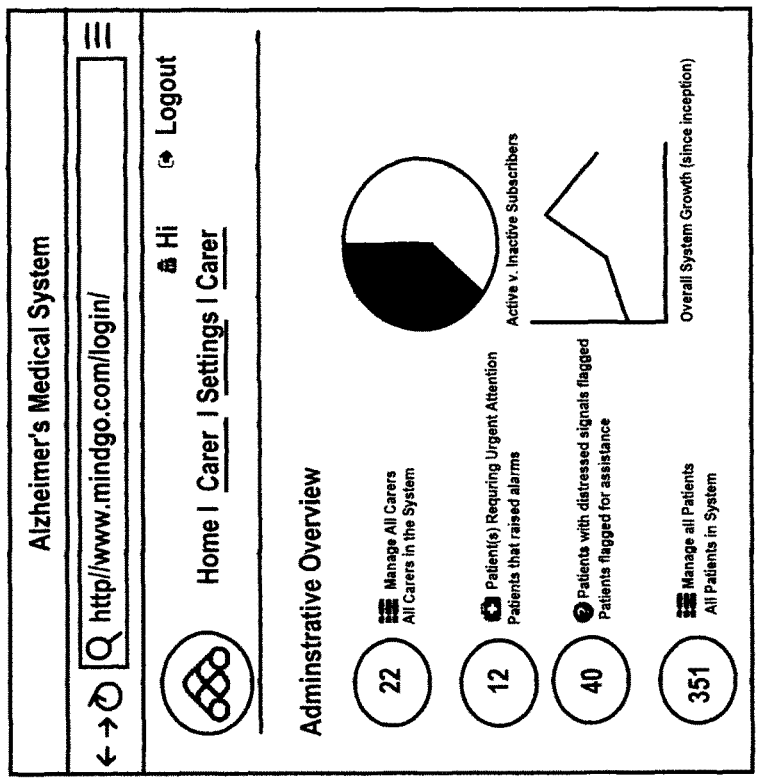
Figure 5A:
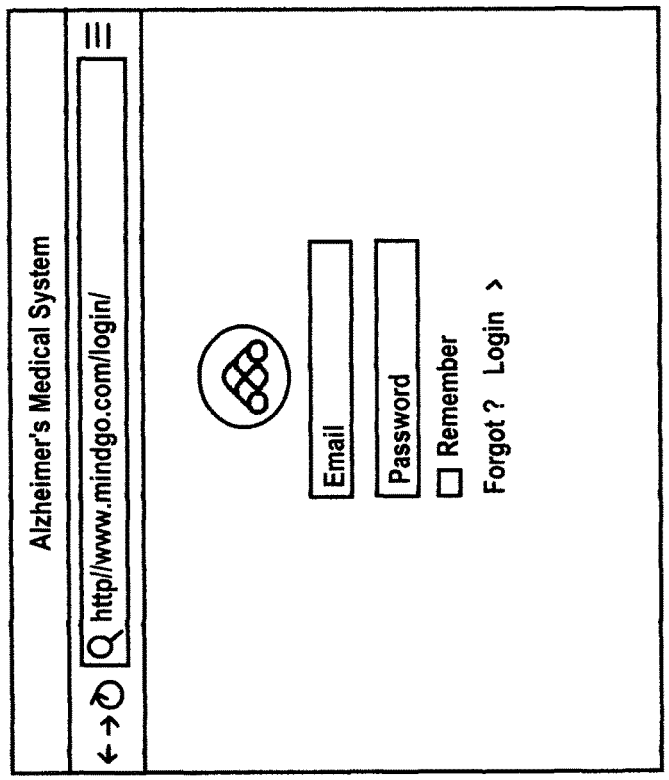

Particularly, FIG. 5A shows the login screen for the administrator while FIG. 5B shows the MindGo system dashboard overview with useful statistics for administrators after they login to the system.

Figure 6B:
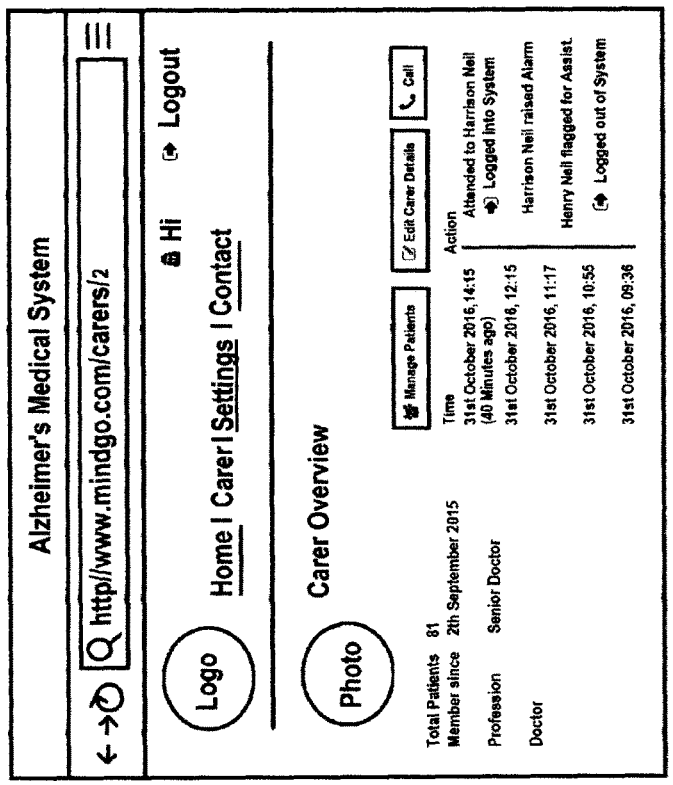
Figure 6A:
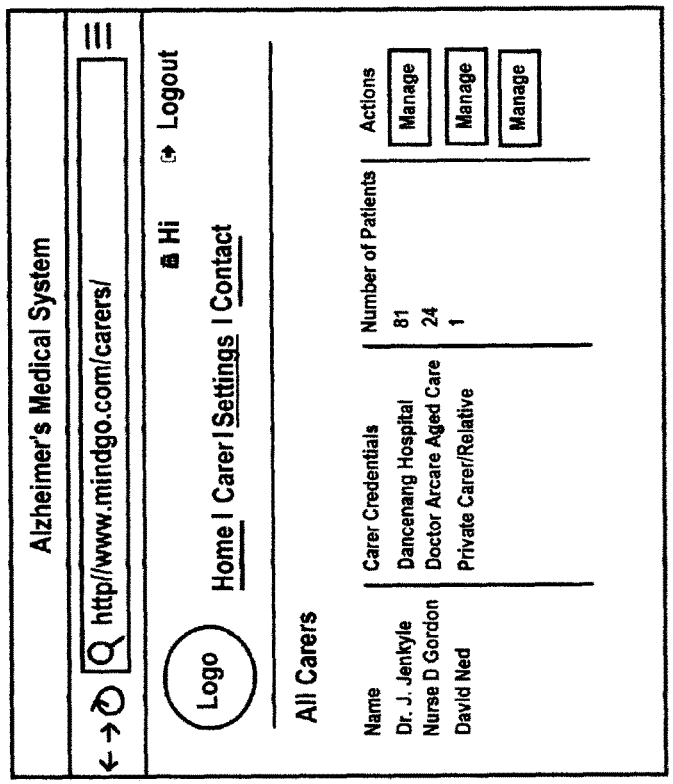

In FIG. 6, additional web pages are disclosed for the MindGo system administrative interfaces. Particularly, FIG. 6A shows the list of carers assigned to an administrator with statistics to assist in their management while FIG. 6B shows the carer overview window, after an administrator has clicked on the "Manage" button for a particular carer in the window of FIG. 6A, disclosing a detailed screen listing various the various carers assigned to an administrator listing the tasks that can be performed.

Figures 7A, 7B:
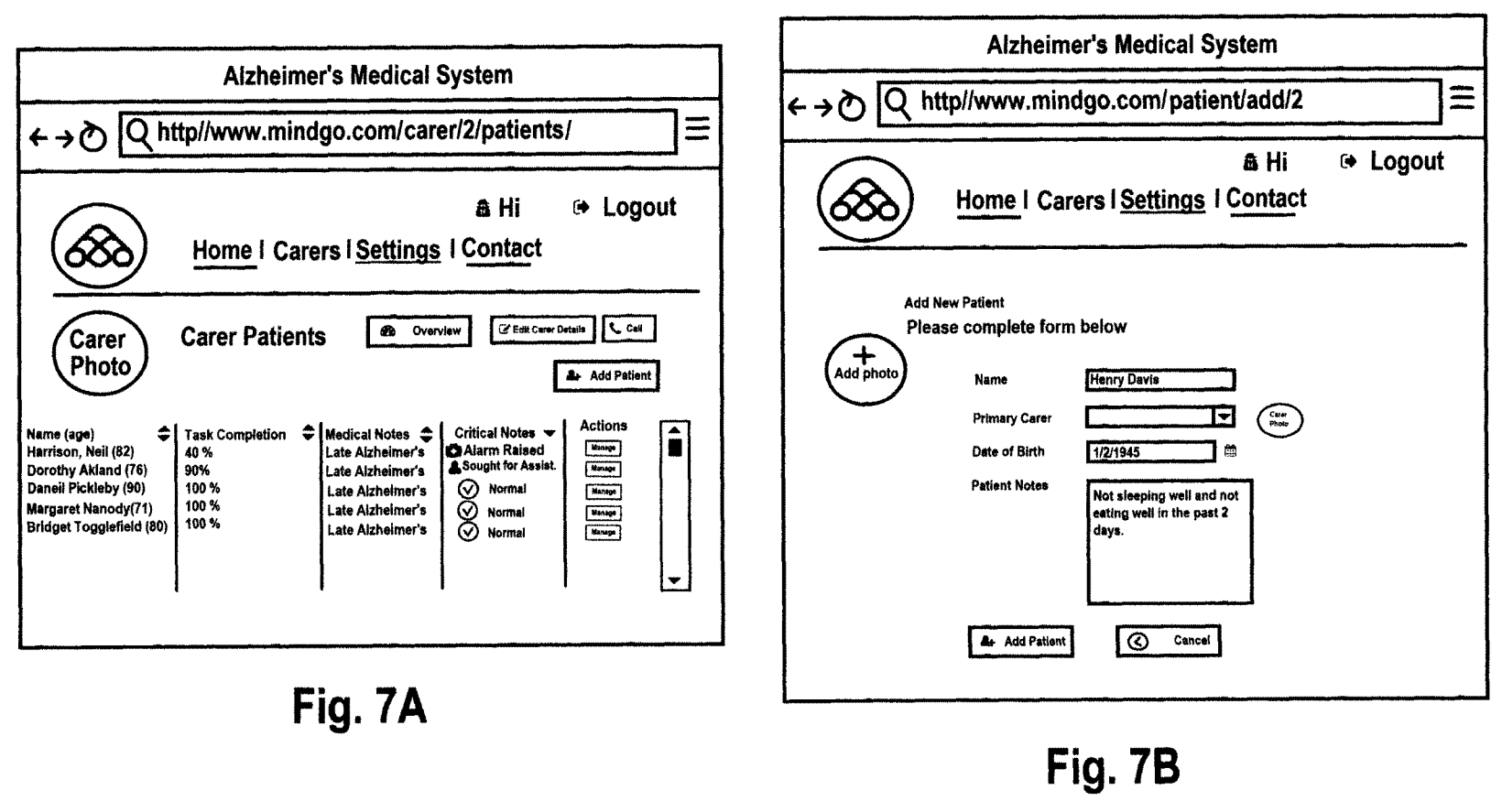

In FIG. 7, additional web pages are disclosed for the MindGo system administrative interfaces. In FIG. 7A a window is shown when an administrator clicks on "Manage Patients", of the window of FIG. 6B, revealing the list of patients/users a carer is responsible for and/or has assigned to them. Finally, in FIG. 7B, a window is shown which allows an administrator to add a patient/user or an edit form is provided to allow for the editing of an existing patient/user.

FIGS. 8 to 12 shows details of the MINDGO system internet web page carer interface and particularly shows how the internet web page carer interface which allows carers to login and manage patients that they are assigned to care for. When a carer is assigned to care for the particular patient/user, the carer is able to manage and oversee everything about that particular patient/user in addition to being able to as assign certain tasks for the patients/users to complete. Carers also have the ability to communicate directly to the patient they are in charge of, and the patients/users can conversely get in direct contact with the carer through the MindGo app supplied contact methods of the MindGo system and devices.

Figure 8B:
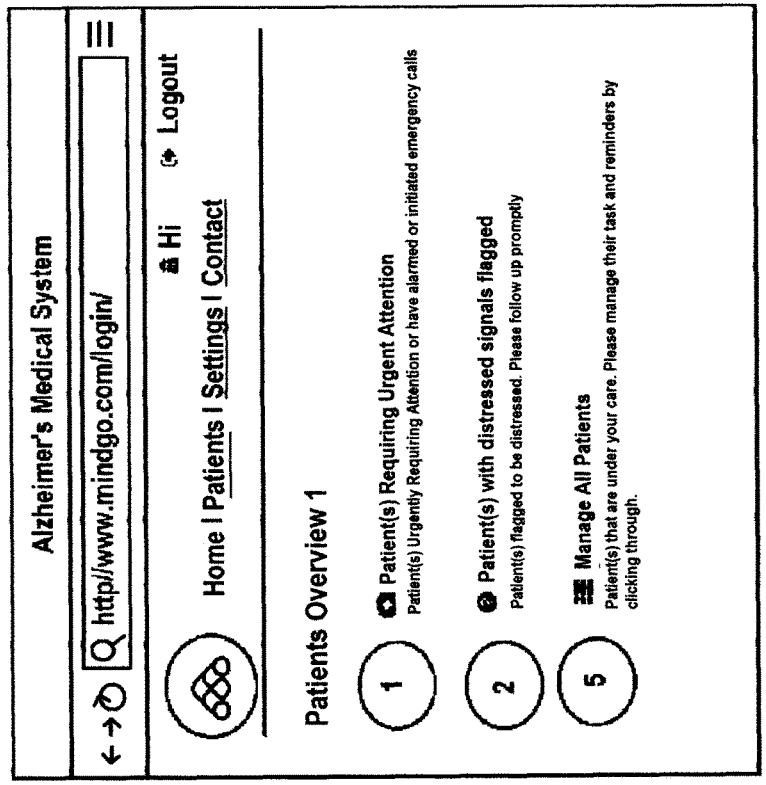
Figure 8A:
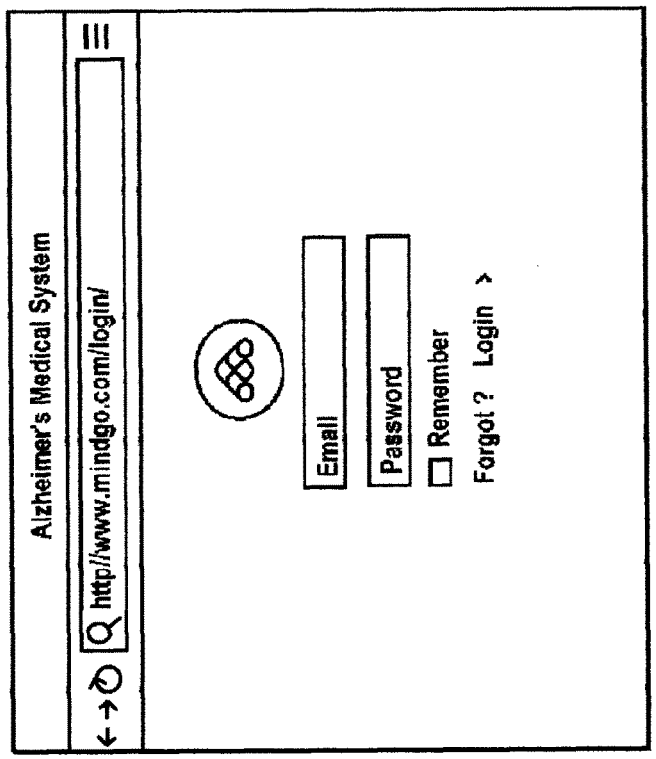

In particularly, FIG. 8A shows the login screen for the carer while FIG. 8B shows the patients overview for the carer after login is successful.

Figures 9A, 9B:
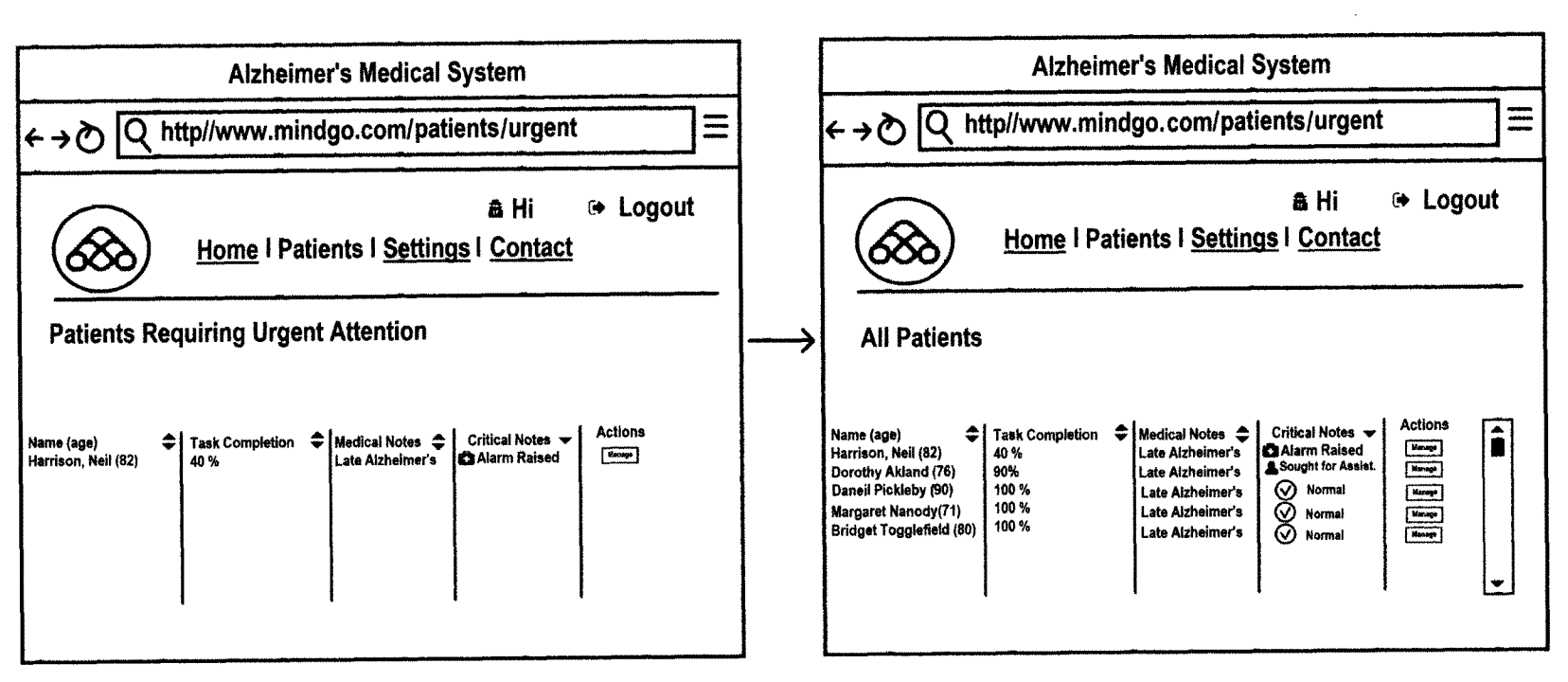

In FIG. 9, additional web pages are disclosed for the MindGo system carer interfaces. Particularly, FIG. 9A shows the list of patients assigned to a carer with a filtered list view of the patients that require urgent attention while FIG. 9b shows all the patients that are currently assign to the carer.

Figure 10B:
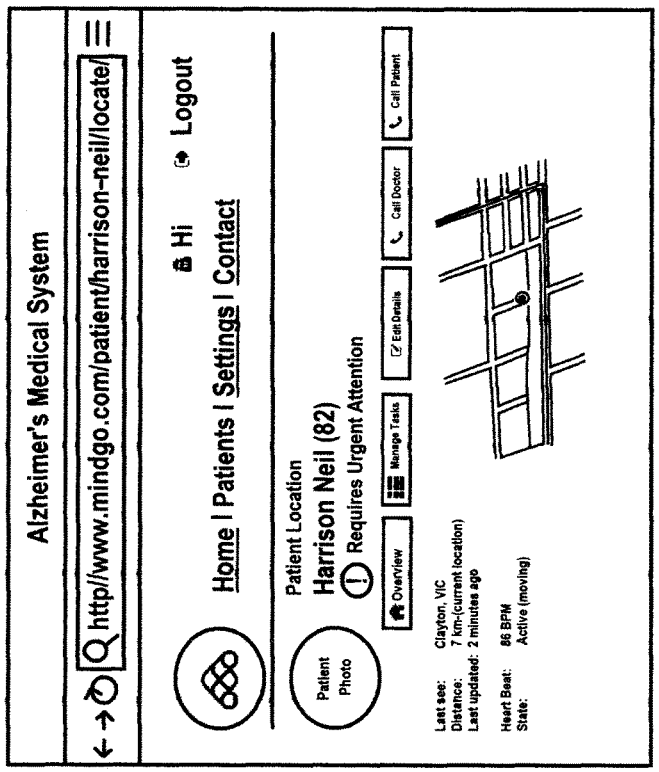
Figure 10A:
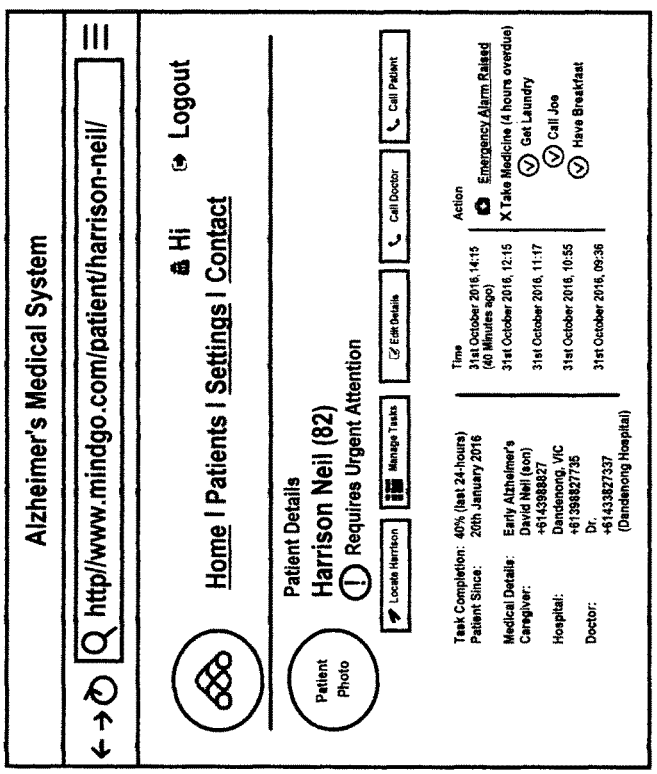

In FIG. 10, additional web pages are disclosed for the MindGo system carer interfaces. In FIG. 10A a window is shown when an carer clicks on "Manage" for a particular patient, in either the window of FIG. 9A or 9B, revealing a detailed view of the patient information and a list of action items for the patient. As shown in FIG. 10B, by clicking on "Locate Harrison" in the window of FIG. 10A, a screen is displayed, for the carer, showing the last location for the patient and various other metric information about the patient.

Figure 11B:
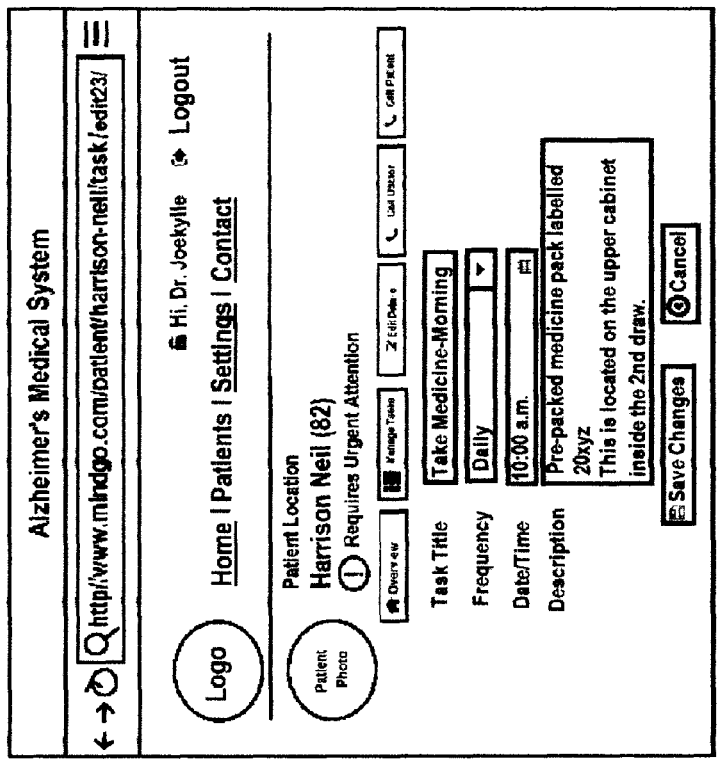
Figure 11A:
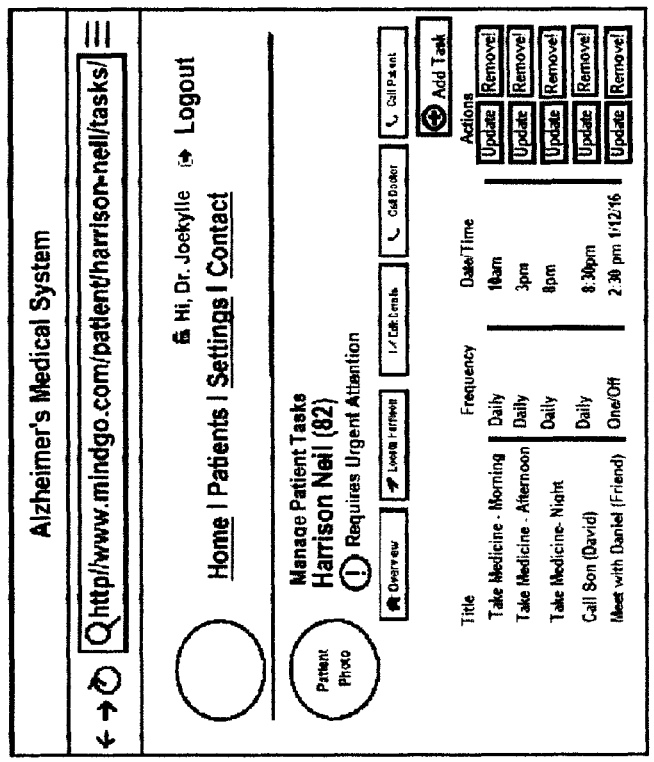

In FIG. 11, additional web pages are disclosed for the MindGo system carer interfaces. In FIG. 11A, if the carer clicks on "Manage Tasks" in either FIG. 10A or 10B, a screen is displayed showing an overview of tasks for the particular patient and operations to edit, add or remove any of the tasks. As shown in FIG. 11B, after clicking on "Update" for a particular task, as shown in the window of FIG. 11A, a screen display is provided allowing a carer to update or adjust a task for the patient.

Figure 12:
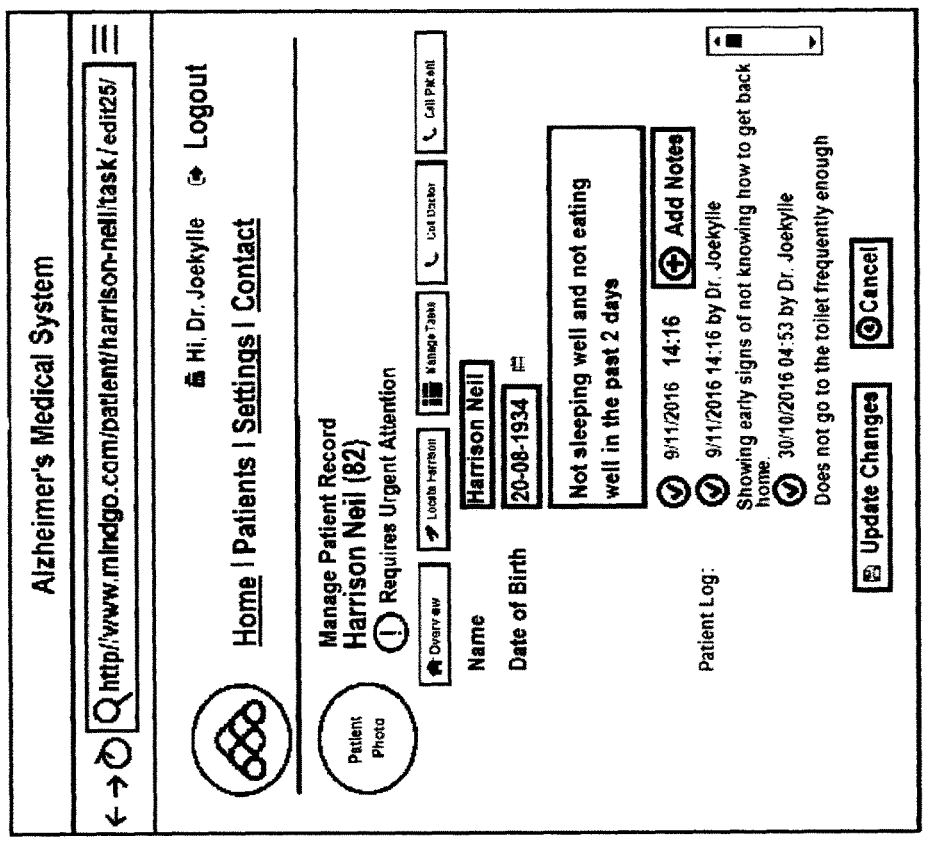
FIG. 12 is an additional schematic of MindGo system internet web page carer interface for the MindGo system and devices of FIGS. 1, 1A-1C, and 2, 2A-2B.

Finally, as shown in FIG. 12, an additional web page is disclosed for the MindGo system carer interfaces. Particularly, after clicking on "Edit Details" of the screens for FIGS. 10A to 11B, a screen is displayed enabling the carer to add medical notes in addition to being edit various patient fields that are applicable for the patient.

Figure 13:
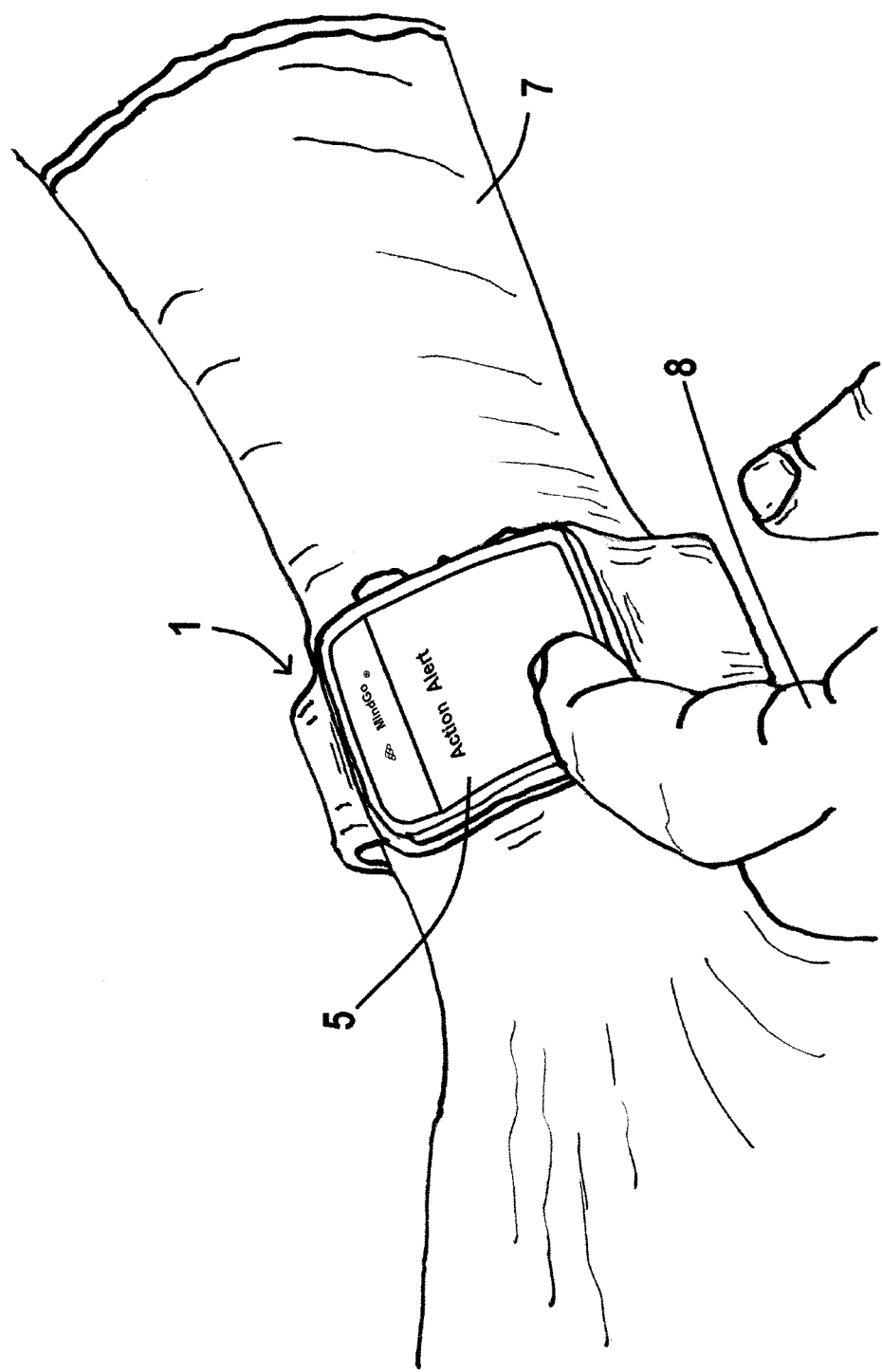
FIG. 13 shows MindGo device of FIGS. 1, 1A-1C in use.

FIG. 13 discloses how the MindGo device 1 in actual use. As shown in FIG. 13, MindGo device 1 is intended to be wore on the wrist 7 of a user and is activated by finger 8 touching various buttons on MindGo device 1. In the example shown in FIG. 12, the user is responding to a prompt "ACTION ALERT".

Figure 14:
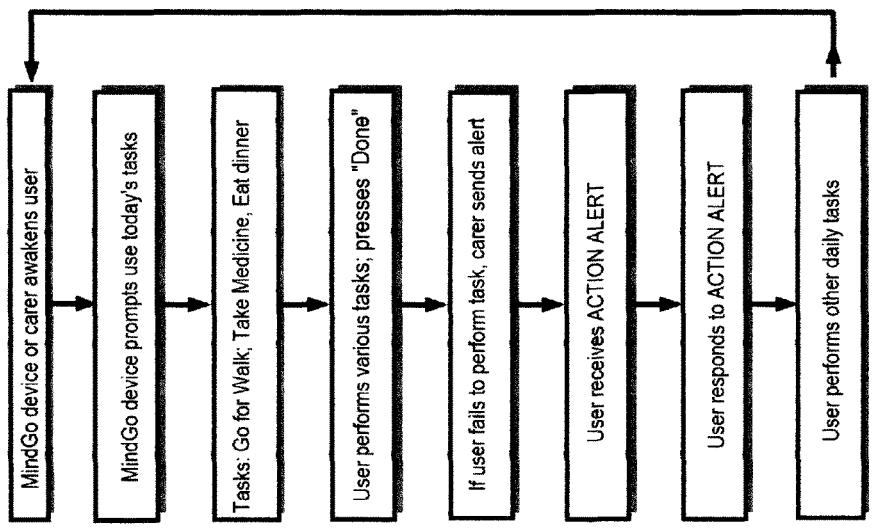
FIG. 14 is a step by step flow chart of an example of various task routines to be prompted by the Mingo system and devices.

FIG. 14 is a step by step flow chart of an example of various task routines to be prompted by the MindGo system and devices for a typical user on a daily basis.

Particularly in FIG. 14 is shown that thru the MindGo device, be it the MindGo device 1 or MindGo device 100, an alarm or carer would awaken the user for a daily routine. The MindGo device would then prompt the User to perform various daily tasks such as "Go for a Walk", "Take Medicine", "Eat Dinner", etc. Once the user performs a particular task, he/she activates the "DONE" button provided on the device. In the event that user fails or neglects to perform a certain task, as monitored by his/her carer, the carer sends an "ACTION ALERT" prompt to user. The user then responds to "ACTION ALERT", performs the task, indicates "DONE", or other action is taken. The user then checks his/her daily calendar for other tasks required for that day. Once all the daily tasks are completed the daily routine would begin the next day.

FIG. 15 discloses in detail, the various screen displays for the MindGo device 1.

Particularly, FIG. 15A shows the display for launching the MindGo app while FIG. 15B shows the display indicating that MindGo app is loading into the MindGo device 1. FIG. 15C shows the home list screen for the user while FIG. 15D reveals an alternative home list screen which can be toggled by a user by force touch on the previous screen display. FIG. 15E is a detailed screen display here prompting the user to "Take Medicine". FIG. 15F is a screen display of detailed "Help Action" list and FIGS. 15G and 15H are screen displays of "ACTION ALERT" reminder for a user here to remind the user to "Take Medicine" and a "DISMISS" feature of the "Action Alert Reminder".

Now referring to FIGS. 16 to 18, the various screen displays for MindGo device 100 similar those of MindGo device 1 are shown.

Particularly, FIG. 16A shows the display for loading the iPhone app into MindGo device 100 while FIG. 16B shows the display the login screen with the password integration. FIG. 16C shows the welcome screen for the user with all the important details for him or her.

Figures 17A, 17B:
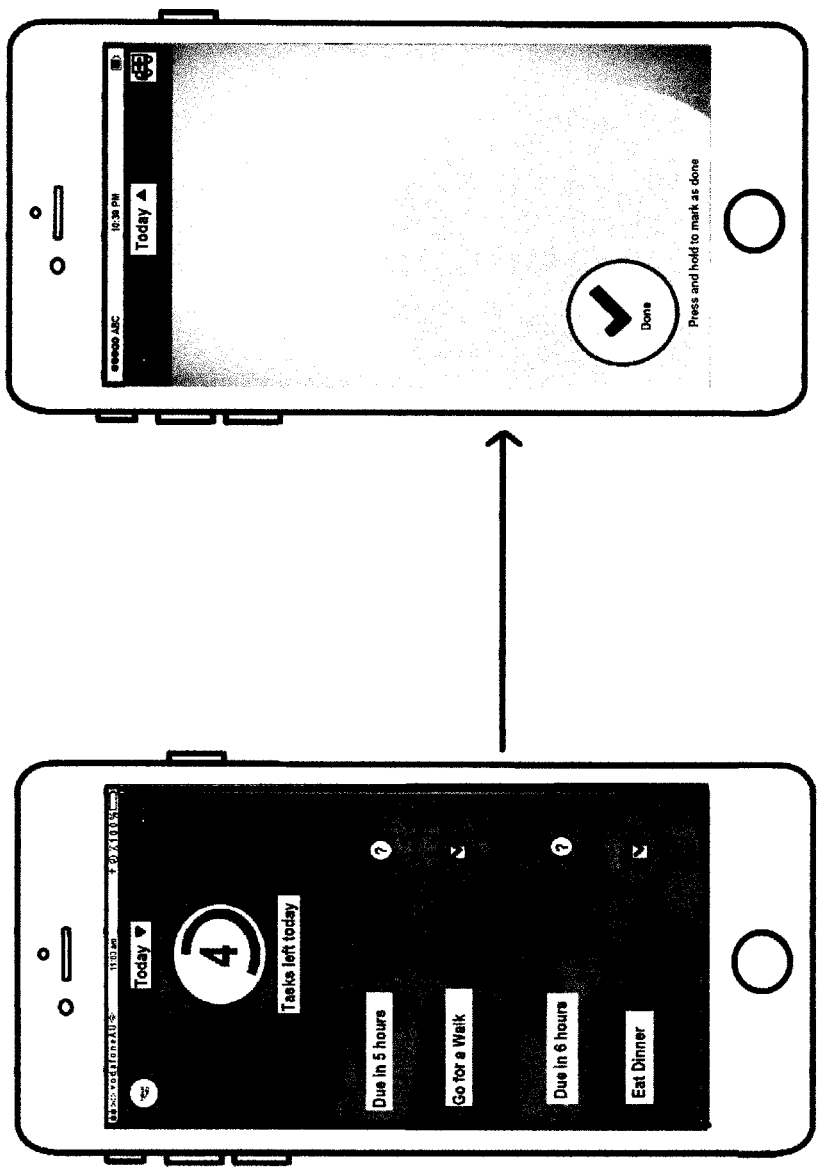

FIG. 17A discloses the home screen display, after authentication by the user, with the daily remainder tasks, due times, and a list of actions for each task. When the user desires to mark a task as completed, he or she needs to tap the "DONE" button for 2-3 seconds on the screen of FIG. 17A until a "Done bubble", as displayed in FIG. 17B, engulfs the entire MindGo device 100 screen. This particular "Done bubble" feature is a preventative measure to ensure and confirm that the user actually desires to mark the task as completed.

Figures 18A, 18B:
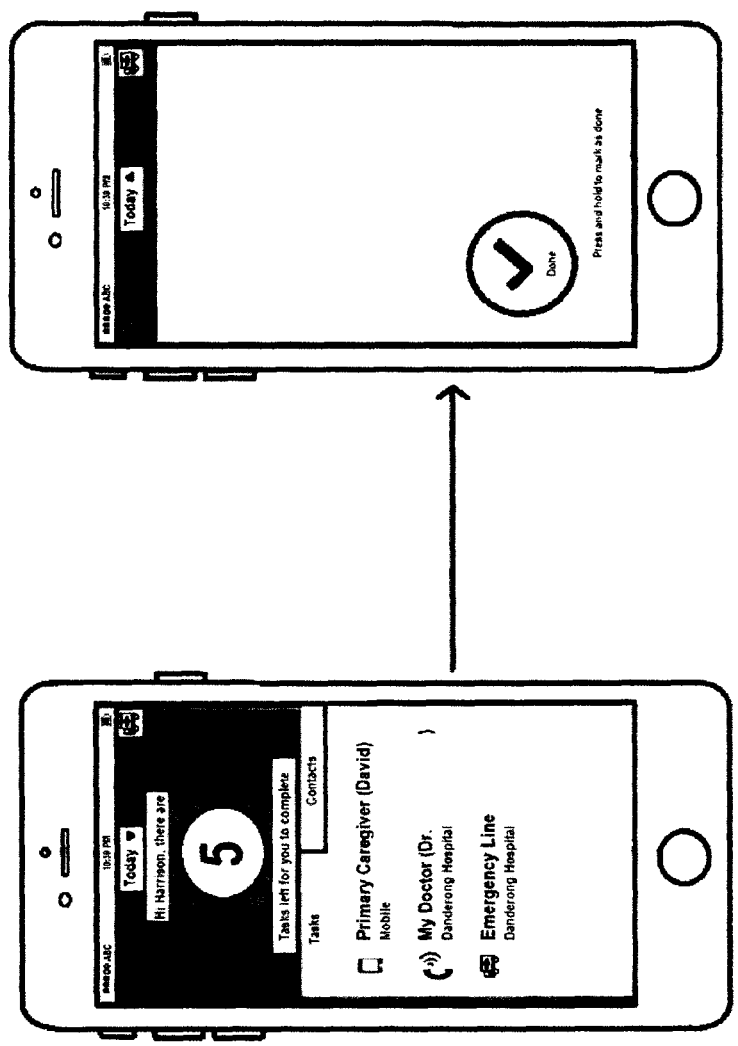

FIG. 18A is a screen display of various important contacts for the user, for example, their primary caregiver or carer, their doctor, or an emergency line, which the user can use to call with a one touch feature while FIG. 18B shows a display confirmation screen when the user taps on a contact from display screen 18A, with a "Call Now" option being displayed to allow the user to make the call to the desired contact.

Finally, referring to FIG. 19, additional screen displays for the MindGo device 100 similar those of MindGo device 1 are shown.

Particularly, FIG. 19A shows the screen that is displayed when a user taps or touches the "Today" button of screen display of FIG. 17A, 17B, 18A or 18B, which brings up a date selector, with task counts of each selector, and with the task count for each day in the future. In addition, tasks missed in the past are displayed in different bubble colors.

FIG. 19B shows the display screen if the user taps or touches the setting icon, denoted as a wheel symbol, in the upper left hand corner of the screen of FIG. 17A, 17B, 18A, 18B, or 19A, a "Settings" screen is displayed.

FIG. 19C is an alternative display screen for settings, in this example for "Apple Watch Settings".

The following example, similar to that FIG. 14, of how the MindGo system and devices can be utilized for a typical user's daily routine are now described. The MindGo device is pre-set by selecting an initial operation, by example, an alarm for the user to be awoken. The alarm may sound aloud on alarm set to start the beginning of the day regarding a routine and for what is a suitable time, for the user, for their day to commence, e.g., 8 a.m. This alarm at 8 a.m. would activate such that the user can hear or see various commands such as "get up out of bed", a "greeting with the time of day and the date", etc. Alternatively, a carer may awaken user. Additionally, the MindGo device would then prompt the user with a list of tasks, such a "Go for a Walk", "Take Medicine" "Eat Breakfast", "Eat Dinner", etc., which could be reinforced with daily check list. In the event the user fails or neglects to complete a task, the carer can send him/her an "ACTION ALERT" reminder. Finally, if the user determines that he/she needs assistance, the user can easily use the contacts button, as previously described, to call a carer.

When introducing elements of the present invention or the preferred embodiment(s) thereof, the articles "a", "an", "the", and "said" are intended to mean there are one or more of the elements. The terms "comprising", "including", and "having" are intended to be inclusive and mean that there may be additional elements other than the listed elements. Also, the term "patient" denotes a person who has been diagnosed or identified as having dementia or similar conditions, for the purposes of the instant invention, and for whom medical care has been prescribed and/or identified while the term "user" denotes a person using the MindGo system and/or devices as described in the instant invention. Similarly, the term "carer" refers to any number of health professionals and/or other individuals involved with providing any time of care, mental, physical, or otherwise for a "user" and/or "patient" and occasionally "patient/user". Additionally, any description of the exemplary or preferred embodiments is intended to be read in connection with the accompanying drawings, which are to be considered part of the entire written description.

Additionally, the principles of the invention could be practiced by those of skilled in the art with equivalent alternative constructions. Although the present invention has been described in considerable detail with reference to a certain preferred embodiment thereof, other embodiments are possible. Therefore, the spirit and scope of the appended claims should not be limited to the description of the preferred embodiment(s) contained herein. The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed:

1. A wearable digital command prompting device for use by a user, comprising
    a digital watch and wherein
    the digital watch is attached to a wrist band and wherein
    the digital watch is capable of being worn by the user and wherein
    the digital watch is provided with a display screen and wherein
    the digital watch is provided with computer processing application software capable of processing any signal, data, or input to or from the digital watch and wherein
    the digital watch is capable of electronically communicating with a mobile device telecommunications network capable of connecting the digital watch to a computer system and wherein
    the digital watch is capable of communicating with the computer system for operating and processing the computer application software and wherein
    the software is capable of producing a command or a prompt on the screen display of the digital watch and wherein
    the command or prompt comprises information, a reminder, or an instruction to inform, remind or command the user to perform a certain task and wherein
    the mobile device telecommunications network is capable of connecting the digital watch to a global positioning satellite system or a global navigational satellite system capable of determining the location of the digital watch and wherein
    the digital watch is an Apple™ digital watch and wherein
    the digital watch is provided with means for causing the digital watch to vibrate to act in an alarm or awakening mode and wherein
    the digital watch is provided with means for causing the digital watch to produce a sound command and wherein
    the computer system is provided with an administrative internet web page interface and wherein the computer application software operates the administrative internet web page interface and wherein
    the administrative internet web page interface is capable of providing a number of computer window displays allowing an administrator to operate the administrative internet web page interface and
    the computer system is provided with a carer internet web page interface and wherein the computer application software operates the carer internet web page interface and wherein
    the carer internet web page interface is capable of providing a number of different computer window displays allowing a carer to operate the carer internet web page interface and transmit commands or prompts to the user via the mobile device telecommunications network and wherein
    the computer system and computer application software function to enable the administrator or carer to locate the user, if desired, and determine the physical or mental needs of the user and wherein
    the computer system and computer application software function to enable the administrator, using the administrative internet web page interface, and the carer, using the carer internet web page interface, to manage the daily activities of the user by a preparing and sending, as needed, a prompt or command on the screen display of the digital watch to the user to inform, remind or command the user to perform a certain task and wherein
    the computer system and digital watch are provided with emergency contact information to allow the user to contact the carer or administrator or an emergency staff location and wherein
    the computer system is provided with a centralized database and the computer application software is capable of processing information and data to and from the centralized database regarding the user to assist the management of the physical and medical needs of the user.

2. A digital command prompting device for use by a user comprising
    a smartphone and wherein
    the smartphone is provided with a display screen and wherein
    the smartphone is provided with computer processing application software capable of processing any signal, data, or input to or from the smartphone and wherein the smartphone is capable of electronically communicating with a mobile device telecommunications network capable of connecting the smartphone to a computer system and wherein the smartphone is capable of communicating with the computer system for operating and processing the computer application software and wherein the software is capable of producing a command or a prompt on the screen display of the smartphone and wherein the command or prompt comprises information, a reminder, or an instruction to inform, remind or command the user to perform a certain task and wherein the mobile device telecommunications network is capable of connecting the smartphone to a global positioning satellite system or a global navigational satellite system capable of determining the location of the smartphone and wherein the smartphone is an Apple™ smartphone and wherein the smartphone is provided with means for causing the smartphone to vibrate to act in an alarm or awakening mode and wherein the smartphone is provided with means for causing the smartphone to produce a sound command and wherein the computer system is provided with an administrative internet web page interface and wherein the computer application software operates the administrative internet web page interface and wherein the administrative internet web page interface can provide a number of computer window displays allowing an administrator to operate the administrative internet web page interface and the computer system is provided with a carer internet web page interface and wherein the computer application software operates the carer internet web page interface and wherein the carer internet web page interface can provide a number of different computer window displays allowing a carer to operate the carer internet web page interface and transmit commands or prompts to the user via the mobile device telecommunications network and wherein the computer system and computer application software function to enable the administrator or carer to locate the user, if desired, and determine the physical or mental needs of the user and wherein the computer system and computer application software function to enable the administrator, using the administrative internet web page interface, and the carer, using the carer internet web page interface, to manage the daily activities of the user by a preparing and sending, as needed, a prompt or command on the screen display of the smartphone to the user to inform, remind or command the user to perform a certain task and wherein the computer system and smartphone are provided with emergency contact information to allow the user to contact the carer or administrator or an emergency staff location and wherein the computer system is provided with a centralized database and the computer application software is capable of processing information and data to and from the centralized database regarding the user to assist the management of the physical and medical needs of the user.

3. A digital command prompting device for use by a user, comprising a mobile electronic device wherein the mobile electronic device is provided with a display screen and wherein the mobile electronic device is provided with computer processing application software capable of processing any signal, data, or input to or from the mobile electronic device and the software can produce a command or a prompt on the screen display of the mobile electronic device and wherein the mobile electronic device is capable of electronically communicating with a mobile device telecommunications network capable of connecting the mobile electronic device to a computer system and wherein the mobile electronic device can communicate with the computer system for operating and processing the computer application software and wherein the mobile electronic device comprises a wearable digital watch attachable to a wrist and wherein the digital watch is capable of being worn by the user and wherein the digital watch is an Apple™ digital watch and wherein the mobile device telecommunications network can connect the digital watch to a global positioning satellite system or a global navigational satellite system capable of determining the location of the digital watch and wherein the digital watch is provided with means for causing the digital watch to vibrate to act in an alarm or awakening mode and wherein the digital watch is provided with means for causing the digital watch to produce a sound command and wherein the command or prompt comprises information, a reminder, or an instruction to inform, remind or command the user to perform a certain task and wherein the computer system and computer application software function to enable an administrator or carer to locate the user, if desired, and determine the physical or mental needs of the user and wherein the computer system and computer application software are provided with an administrative internet web page interface and wherein the computer application software operates the administrative internet web page interface and wherein the administrative internet web page interface can provide a number of computer window displays allowing the administrator to operate the administrative internet web page interface and wherein the computer system and computer application software are provided with a carer internet web page interface and wherein the computer application software operates the carer internet web page interface and wherein the carer internet web page interface can provide a number of computer window displays allowing the carer to operate the carer internet web page interface the computer system and computer application software function to enable the administrator and the carer, to manage the daily activities of the user by a preparing and sending, as needed, a prompt or command on the screen display of the mobile electronic device to the user to inform, remind or command the user to perform a certain task to assist the management of the physical and medical needs of the user.

4. The digital command prompting device of claim 3 wherein the computer system and digital watch are provided with emergency contact information to allow the user to contact the carer or administrator or an emergency staff location.

5. The digital command prompting device of claim 4 wherein the computer system is provided with a centralized database and the computer application software is capable of processing information and data to and from the centralized database regarding the user to assist the management of the physical and medical needs of the user.

6. A digital command prompting device for use by a user, comprising a mobile electronic device wherein the mobile electronic device is provided with a display screen and wherein the mobile electronic device is provided with computer processing application software capable of processing any signal, data, or input to or from the mobile electronic device and wherein the mobile electronic device is capable of electronically communicating with a mobile device telecommunications network capable of connecting the mobile electronic device to a computer system and wherein the mobile electronic device can communicate with the computer system for operating and processing the computer application software and wherein the software can produce a command or a prompt on the screen display of the mobile electronic device and wherein the command or prompt comprises information, a reminder, or an instruction to inform, remind or command the user to perform a certain task and wherein the computer system and computer application software function to enable an administrator or carer to locate the user, if desired, and determine the physical or mental needs of the user and wherein the mobile electronic device comprises a smartphone and wherein the mobile device telecommunications network can connect the smartphone to a global positioning satellite system or a global navigational satellite system capable of determining the location of the smartphone and wherein the smartphone is an Apple™ smartphone and wherein the smartphone is provided with means for causing the smartphone to vibrate to act in an alarm or awakening mode and wherein the smartphone is provided with means for causing the smartphone to produce a sound command and wherein the computer system and computer application software are provided with an administrative internet web page interface and wherein the computer application software operates the administrative internet web page interface and wherein the administrative internet web page interface is capable of providing a number of computer window displays allowing the administrator to operate the administrative internet web page interface and wherein the computer system and computer application software are provided with a carer internet web page interface and wherein the computer application software operates the carer internet web page interface and wherein the carer internet web page interface can provide a number of computer window displays allowing the carer to operate the carer internet web page interface and wherein the computer system and computer application software function to enable the administrator and the carer, to manage the daily activities of the user by a preparing and sending, as needed, a prompt or command on the screen display of the mobile electronic device to the user to inform, remind or command the user to perform a certain task to assist the management of the physical and medical needs of the user.

7. The digital command prompting device of claim 6 wherein the computer system and smartphone are provided with emergency contact information to allow the user to contact the carer or administrator or an emergency staff location.

8. The digital command prompting device of claim 7 wherein the computer system is provided with a centralized database and the computer application software is capable of processing information and data to and from the centralized database regarding the user to assist the management of the physical and medical needs of the user.

\* \* \* \* \*